United States Patent [19]

Idaka

[11] Patent Number: 4,999,423
[45] Date of Patent: Mar. 12, 1991

[54] ACYLATED ANTHOCYANIN AND PROCESS FOR PRODUCING THE SAME AS WELL AS PIGMENT COMPOSITION CONTAINING THE SAME

[75] Inventor: Eiichi Idaka, Gifu, Japan

[73] Assignee: Suntory Limited, Osaka, Japan

[21] Appl. No.: 167,269

[22] Filed: Mar. 11, 1988

[51] Int. Cl.$^5$ .................... C07G 3/00; C07H 15/00; C07H 17/04
[52] U.S. Cl. ........................ 536/4.1; 536/8; 536/8.8; 536/18.1
[58] Field of Search ............... 536/4.1, 18.1, 8, 8.8; 106/498

[56] References Cited

U.S. PATENT DOCUMENTS 4,211,577  7/1980  Wallin .............................. 106/498

OTHER PUBLICATIONS

Idaka et al., "Structure of Zebrinin, A Novel Acylated Anthocyanin Isolated from *Zebrina Pendula*", Tetrahedron Letters, vol. 28, No. 17 (1987), pp. 1901–1904.

Primary Examiner—Amelia Burgess Yarbrough
Attorney, Agent, or Firm—Cushman, Darby & Cushman

[57] ABSTRACT

A novel acylated anthocyanin of the formula:

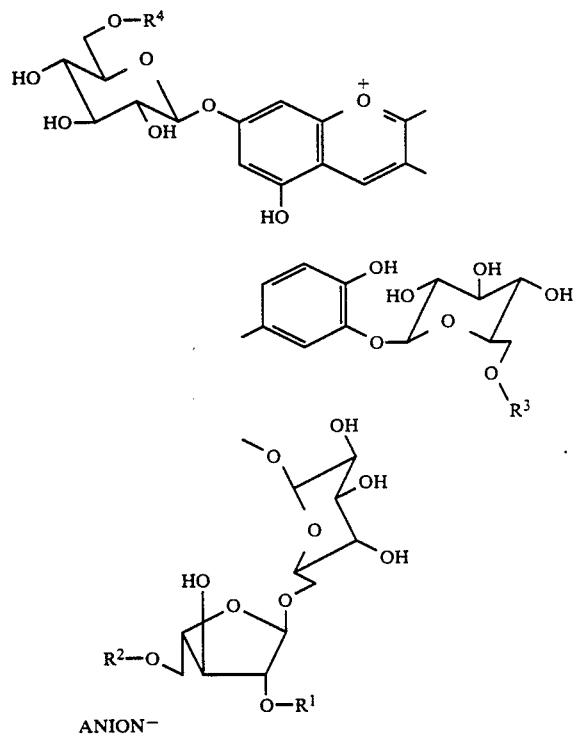

(wherein $R^1$ and $R^2$ may be the same or different and each represents a hydrogen atom, a ferulyl group or a caffeyl group; $R^3$ and $R^4$ may be the same or different and each represents a ferulyl group or a caffeyl group; and ANION$^-$ represents an anion) and a process for producing the same, as well as a pigment composition containing said anthocyanin.

9 Claims, 1 Drawing Sheet

ACYLATED ANTHOCYANIN AND PROCESS FOR PRODUCING THE SAME AS WELL AS PIGMENT COMPOSITION CONTAINING THE SAME

FIELD OF THE INVENTION:

The present invention relates to an acylated anthocyanin of the formula (I):

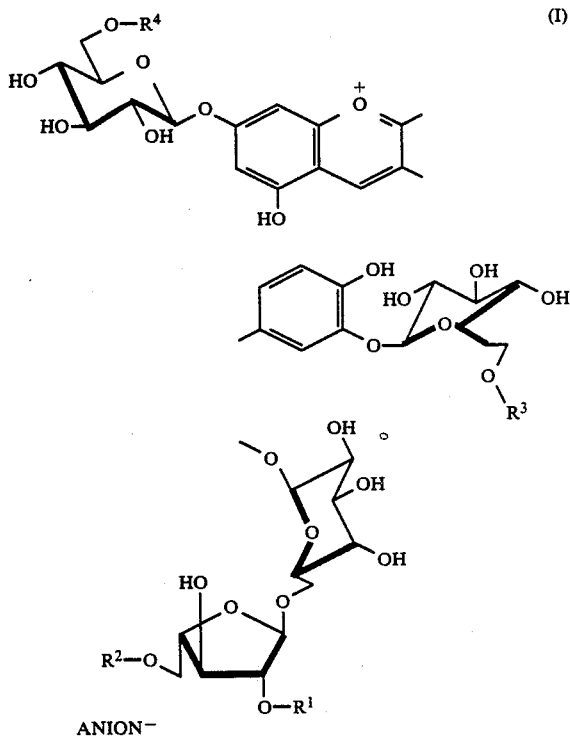

(wherein $R^1$ and $R^2$ may be the same or different and each represents a hydrogen atom, a ferulyl group or a caffeyl group; $R^3$ and $R^4$ may be the same or different and each represents a ferulyl group or a caffeyl group; and ANION⁻ represents an anion) and a process for producing the same. The present invention also pertains to a pigment composition containing said anthocyanin.

Acylated anthocyanins according to the present invention are pigments derived from a natural source, have markedly superior stability and therefore are useful as coloring agents for foods, pharmaceuticals, cosmetics, etc.

PRIOR ART

Anthocyanidins of the formula (II):

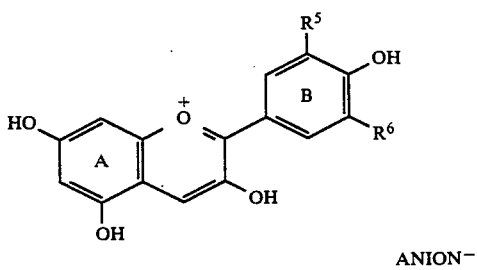

(wherein $R^5$ and $R^6$ may be the same or different and each represents a hydrogen atom, hydroxyl group or methoxy group) are well known [see e.g., Developments in Food Colours-I, edited by John Walford (1980), Applied Science Publishers Ltd., London, or The Flavonoids, edited by J. B. Harborne, T. J. Mabry and H. Mabry (1975, 1983), Chapman & Hall Ltd.]

Anthocyanins of the formula (III):

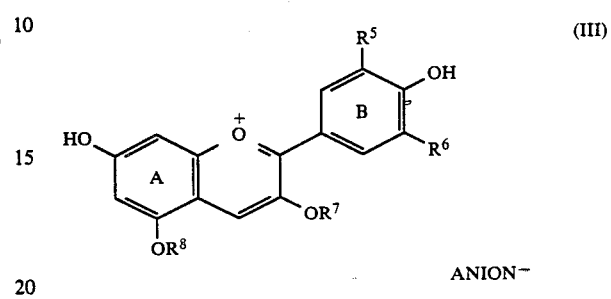

(wherein $R^5$ and $R^6$ are as defined above; $R^7$ represents a glycosyl or acyl-glycosyl group; and $R^8$ represents a hydrogen atom or a glycosyl group), which comprise a sugar component attached to the anthocyanidins of the formula (II), are contained in large quantities in purple corn, berries, the rind of grapes, grape juice, red cabbage and the like. Therefore, pigments which are produced by steeping the flowers, leaves, stems or fruits of these plants in water or an aqueous alcohol solution containing an acid are widely used as coloring agents for beverages, foods, candies, etc. see Takeshi Umeda "Sanei News" No. 143 (1983), Sanei Kagaku Kogyo, pp. 15-21].

Athocyanins show generally a purplish red to blue color in a dilute aqueous solution at a neutral pH, but they are generally unstable and rapidly discolor under neutral to alkaline conditions, although under acidic conditions they are relatively stable and assume a red to orange color. This is because anthocyanins are present in acidic solutions in the form of flavylium ions represented by the aforementioned formula (III). On the other hand, in aqueous solutions of pH 4-6, anthocyanins are present in the form of anhydro-bases of the formula (IV):

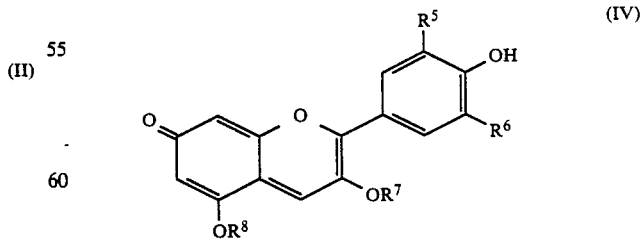

(wherein $R^5$, $R^6$, $R^7$ and $R^8$ are the same as those defined above) which are unstable and show a purple or blue color, and the anhydro-bases readily hydrate to form colorless pseudo-bases of the formula (V):

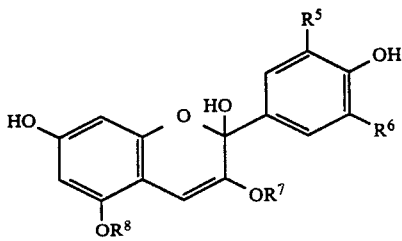

(V)

(wherein $R^5$, $R^6$, $R^7$ and $R^8$ are the same as defined above) [see R. Brouillard and B. Delaporte, J. Am. Chem. Soc., 998461 (1977), or Tsutomu Hoshino "Kagakuno Ryoiki", 37, 23–30 (1983)]. Accordingly, foods and pharmaceuticals that utilize anthocyanin pigments readily lose their color due to the effect of acids or alkalis or in raised temperature conditions under particular circumstances.

SUMMARY OF THE INVENTION

An object of the present invention is to provide a novel acylated anthocyanin which has an attractive color which is red in acidic conditions and is stable at a wide pH range.

Another object of the present invention is to provide a method of obtaining said acylated anthocyanin from natural sources, that are plants.

A further object of the present invention is to provide a pigment composition for foods, pharmaceuticals or cosmetics, etc. which is stable over long periods of time.

DETAILED DESCRIPTION OF THE INVENTION

Figure 1:
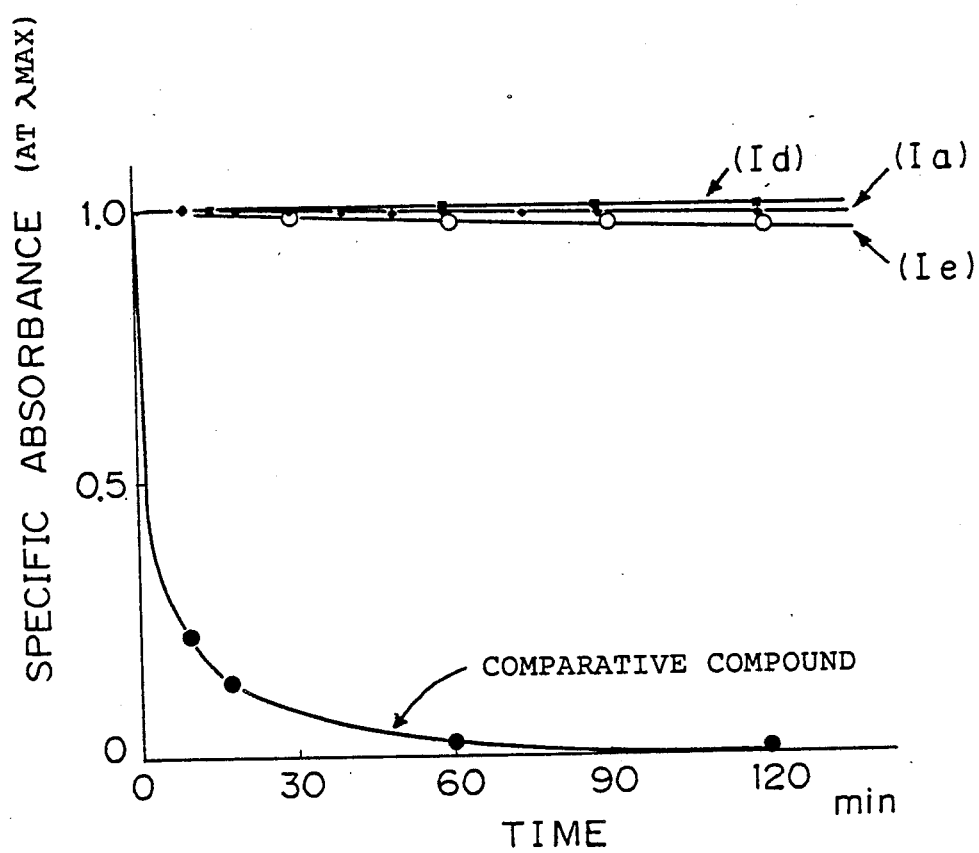
FIG. 1 is a graph showing the results of a comparison between the novel acylated anthocyanins according to the present invention and a comparative anthocyanin [a deacylated derivative of the compound of the formula (I)]in terms of stability in a 1/30 M phosphate buffer solution (pH 6.5).

In view of the above-described problems, the present inventor made exhaustive studies in order to find stable anthocyanins from a wide variety of plants. In the conventional analysis of anthocyanins such as paper chromatography (PPC) or the thin layer chromatography (TLC) on cellulose powder, tailing of the pigments is so heavy that it is difficult to separate them satisfactorily. Even the HPLC method which in general gives high resolution has not been able to give satisfactory separation patterns when applied to anthocyanins.

In these circumstances the inventor thought that if he could establish a method which enables satisfactory separation of anthocyanins he might be able to find stable anthocyanins. Motivated by the above assumption, he developed a novel method of analyzing or separating anthocyanins. Briefly, the method is characterized in that the separation of anthocyanins is conducted in acidic conditions which do not exceed pH 3.5. This novel method enabled clear cut separation of anthocyanins from various types of plants, and the inventor finally found stable types of anthocyanin which form the subject matter of the invention and which are expressed by the above-described formula (I).

The structure of the anthocyanins of the invention is completely different from that of the known anthocyanins since the former is highly acylated by various residues of organic acid (these stable anthocyanins of the invention will be hereinafter referred to as "acylated anthocyanins"). The present invention has been accomplished on the basis of this finding. As to acylated anthocyanins, the only four known ones are gentiodelphin, platyconin, cinerarin and HBA (see Toshio Goto and Tadao Kondo "Kagaku to Seibutsu", Vol. 22, p. 827, 1984). However, the known acylated anthocyanins have very complicated structures which are completely different from the basic structure of the novel acylated anthocyanins of the formula (I). On top of that, even though HBA is nearly as stable as the acylated anthocyanins of the invention, the natural sources of HBA is too limited to obtain them on commercial bases. All the other three of the known acylated anthocyanins are not stable.

A novel acylated anthocyanin according to the present invention may be produced by the following process.

For example, the flowers, leaves or stems of Zebrina purpusii Bruechen belonging to Commelinaceae are ground. Then, the resulting powder is steeped in an alcoholic solvent or aqueous solvent which contains an acid to carry out extraction, and the extract thus obtained is filtered and then dried in vacuum, thereby obtaining an oily crude acylated anthocyanin. There are three different methods of purifying this crude acylated anthocyanin, that is, ether precipitation, purification by means of an adsorption column, and liquid chromatography employing a counter current partition column. For example, in the liquid chromatography method, the crude acylated anthocyanin is purified by a high performance liquid chromatography (HPLC) that employs a counter current partition column [an octyl ($C_8$) column, octadecyl ($C_{18}$) column, etc.] with a mobile phase which comprises a mixed solvent composed of two or more elements selected from the group consisting of acetic acid, acetonitrile, tetrahydrofuran (THF), dioxane, alcohols and water, and which further contains about 0–5% of a mineral acid, organic acid or the like as an acid so that the pH value of the mobile phase is in the range of 3.5–0, thereby obtaining a pure acylated anthocyanin (Ia) [a compound of the formula (I), wherein each of $R^1$, $R^2$, $R^3$ and $R^4$ represents a caffeyl group], i.e., 3-O-{6-O-(2,5-di-O-E-caffeyl-α-L-arabinofuranosyl)-β-D-glucopyranosyl}-7-O-(6-O-E-caffeyl-β-D-glucopyranosyl)-3'-O(6-O-E-caffeyl-β-D-glucopyranosyl)cyanidin. (Ia)

This acylated anthocyanin (Ia) is identified by a peak which appears at a retention time (RT) of about 10 minutes in the HPLC analysis (column: Develosil ODS-C5, manufactured by Nomura Kagaku Kenkyusho Ltd., Japan, 250 mm×4.6 mm I.D.; column temperature: 40° C.; mobile phase: a mixed solvent of acetic acid, acetonitrile, phosphoric acid and water mixed in the proportion 10:11:1.5:77.5) conducted using a UV detector.

By similarly extracting, separating and purifying the flowers, leaves or stems of the plant Zebrina pendula Schnitzlein, it is possible to isolate as the major pigments the above-described acylated anthocyanin (Ia) and two other novel acylated anthocyanins, that is, an acylated anthocyanin (Ib) [a compound of the formula (I), wherein $R^1$ represents a hydrogen atom; and each of $R^2$, $R^3$ and $R^4$ represents a caffeyl group], i.e., 3-O-{6-O-(5-O-E-caffeyl-α-L-arabinofuranosyl)-β-D-glucopyranosyl}-7-O-(6-O-E-caffeyl-β-D- glucopyranosyl)-3'-O-(6-O-E-caffeyl-β-D-glucopyranosyl)cyanidin, (Ib)
and an acylated anthocyanin (Ic) [a compound of the formula (I), wherein $R^2$ represents a hydrogen atom; and each of $R^1$, $R^3$ and $R^4$ represents a caffeyl group], i.e.
3-O-{6-O-(2-O-E-caffeyl-α-L-arabinofuranosyl)-β-D-glucopyranosyl}-7-O-(6-O-E-caffeyl-β-D-glucopyranosyl)-3'-O-(6-O-E-caffeyl-β-D-glucopyranosyl)cyanidin. (Ic)

By similarly processing the plant Setcreasea purpurea BOOM, it is possible to isolate as a main pigment a novel acylated anthocyanin (Id) [a compound of the formula (I), wherein $R^1$, $R^2$, $R^3$ and $R^4$ represent ferulyl group], i.e.,
3-O-{6-O-(2,5-di-O-E-ferulyl-α-L-arabinofuranosyl)-β-D-glucopyranosyl}-7-O-(6-O-E-ferulyl-β-D-glucopyranosyl)-3'-O-(6-OE-ferulyl-β-D-glucopyranosyl)cyanidin. (Id)

By similarly processing the plant Rhoeo spathaceae W. T. Stearn, it is possible to isolate a novel acylated anthocyanin (Ie) [a compound of the formula (I), wherein $R^1$ represents a hydrogen atom; and each $R^2$, $R^3$ and $R^4$ represents a ferulyl group], i.e.,
3-O-{6-O-(5-O-E-ferulyl-α-L-arabinofuranosyl)-β-D-glucopyranosyl}-7-O-(6-O-E-ferulyl-β-D-glucopyranosyl)-3'-O-(6-O-E-ferulyl-β-D-glucopyranosyl)cyanidin. (Ie)

The acylated anthocyanins of the invention cause no health hazards since they are components of edible plants. This safeness in combination with the clear color and the stability of acylated anthocyanins means that they offer great promise for use as pigments in the coloring of pharmaceuticals, foods and cosmetics and the like. The amount of pigment used in said product may be determined by routine tests, but usually 0.01–10% of the pigment on the basis of the total volume of the product will be sufficient to give it a desired color.

The acylated anthocyanin of the invention may be used singly or in combination with one or more suitable carriers and/or additives conventionally used to form a pigment composition. For example, the anthocyanin may be dissolved in a suitable medium preferably at pH 3–8.

The present invention will be explained more specifically below by way of Examples. However, the present invention is in no way restricted to these Examples.

EXAMPLE 1

Fresh leaves (6.4 kg) of Zebrina purpusii was placed in liquid nitrogen, and the frozen leaves were immediately ground and then steeped in 5.3 l of methanol containing 1% hydrochloric acid for 15 hours at 4° C. to extract pigments. The extraction with 3 l of the acidic methanol under the same condition was repeated with the extraction residue. The two batches of the extracted solution were combined and left to stand overnight at an ambient temperature and the precipitates formed were then filtered off. The filtrate was mixed with 26.5 l of water and the mixed solution was subjected to an Amberlite XAD−7 column (560 mm×80 mm I.D.) which had been equilibrated with water. The column was washed with 1l of 40% aqueous methanol and the successively eluted with 45% aqueous methanol (0.5 l), 50% aqueous methanol (0.5 l), 55% aqueous methanol (0.5 l), 65% aqueous methanol (6 l), 75% aqueous methanol (5 l), 80% aqueous methanol (1 l) and methanol (3 l) each of which contains 0.5% TFA. The fraction of 65% aqueous methanol containing 0.5% TFA was collected followed by concentration under a reduced pressure. The residue was dissolved in a small amount of methanol containing 1% HCl. Five volume of ether was slowly added to the solution to precipitate the pigments which were then collected to obtain about 700 mg of crude anthocyanin. The crude anthocyanin was divided into 70 mg portions and each portion was dissolved in a small amount of 0.5% aqueous TFA and subjected to a purification step by HPLC (column: ODS-C 10/20, 250 mm×10 mm I.D.; mobile phase: acetic acid/acetonitril/TFA/water=5.4:6.8:0.5:87.3), whereby a main pigment component obtained was the acylated anthocyanin of the formula (Ia) [a compound of the formula (I), wherein each of $R^1$, $R^2$, $R^3$ and $R^4$ represents a caffeyl group], i.e.,
[3-O-{6-O-(2,5-di-O-E-caffeyl-α-L-arabinofuranosyl)-β-D-glucopyranosyl]-7-O-(6-O-E-caffeyl-β-D-glucopyranosyl)-3'-O-(6-O-E-caffeyl--β-D-glucopyranosyl)cyanidin].

Analysis: $C_{74}H_{73}O_{37}$=1,553

UV $\lambda_{max}$nm (ε): (0.01% HCl/MeOH, conc., 2.7×10$^{-5}$ mol/l, 20° C.); 532(25,000), 329(51,800), 292(47,300): (1/30 M phosphate buffer, pH 6.5, conc., 2.7×10$^{-5}$ mol/l, 20° C.); 583(28,800), 543(27,100), 506(13,900), 470(5,700), 323(36,500), 306(39,300), 237(36,100)

FAB-MS (m/z):1,553 (M+)

$^1$H-NMR (500 MHz, 3% CF$_3$COOD/CD$_3$OD, −20° C., δ(ppm): 8.40(1H,br.d,J=9.5), 8.28(1H,s), 7.41(1H,d,J=16), 7.37(1H,br), 7.28(1H,d,J=16), 6.99(1H,d,J=9.5), 6.93(2H,d,J=16), 6.91(1H,d,J=1.3), 6.84(1H,d,J=1.3), 6.73(1H,d,J=1.3), 6.65(1H,dd,J=1.3, 8.0), 6.63(1H,d,J=1.3), 6.61(1H,d,J=8.0), 6.59(1H,d,J=8.0), 6.53(1H,d,J=8.0), 6.50(1H,dd,J=1.3, 8.0), 6.26(1H,d,J=1.3), 6.21(1H,d,J=8.0), 6.14(1H,d,J=16), 6.06(1H,d,J=1.3), 6.055(1H,dd,J=1.3, 8.0), 6.05(1H,d,J=16), 5.87(1H,d,J=16), 5.76(1H,d,J=16), 5.75(1H,d,J=16), 5.38(1H,d,J=7.5), 5.20(1H,s), 5.18(1H,d,J=1.3), 5.07(1H,d,J=7.5), 5.03(1H,d,J=7.5), 4.92(1H,dd,J=9.5, 12), 4.45(1H,dd,J=2.0, 12), 4.31(1H,dd,J=5.0, 12), 4.25(1H,m), 4.18(1H,br.d,J=10), 4.02(1H,dd,J=1.3, 9.0), 3.94(1H,br.d,J=12), 3.92(1H,dd,J=7.5, 12), 3.90(1H,br.d,J=12), 3.86(2H,m), 3.81(1H,m), 3.74(1H,m), 3.71(1H,dd,J=7.5, 9.0), 3.71(1H,t,J=9.0), 3.67(1H,dd,J=7.5, 9.0), 3.66(1H,dd,J=7.5, 9.0), 3.65(2H,t,J=9.0), 3.44(1H,t,J=9.0), 3.38(1H,t,J=9.0)

EXAMPLE 2

One kilogram of fresh leaves of Zebrina pendula Schnitzlein was extracted and separated in the same way as in Example 1 to obtain the same acylated anthocyanin (Ia) as that obtained in Example 1 and two other novel acylated anthocyanins that is (Ib):
[3-O-{6-O-(5-O-E-caffeyl-α-L-arabinofuranosyl)-β-D-glucopyranosyl}-7-O-(6-O-E-caffeyl-β-D-glucopyranosyl)-3'-O-(6-O-E-caffeyl-β-D-glucopyranosyl)cyanidin],
and (Ic):
[30-{6-O-(2-O-E-caffeyl-α-L-arabinofuranosyl)-β-D-glucopyranosyl}-7-O-(6-OE-caffeyl-β-D-glucopyranosyl)-3'-O-(6-O-E-caffeyl-β-D-glucopyranosyl)cyanidin].

The structures of (Ib) and (Ic) were identified from the fact that FAB-MS of both of them was m/Z=1.319

(M+)(C$_{65}$H$_{67}$O$_{34}$) from the results of alkaline hydrolysis and acidic partial hydrolysis.

EXAMPLE 3

One kilogram of fresh leaves of Setcreasea purpurea BOOM was processed in the same way as in Example 1 to obtain a novel acylated anthocyanin (Id):

[3-0-(6-0-(2,5-di-0-E-ferulyl-α-L-arabinofuranosyl)-β-D-glucopyranosyl}-7-0-(6-0-E-ferulyl-β-D-glucopyranosyl)-3'-0-(6-0-E-ferulyl-β-D-glucopyranosyl)cyanidin].

Analysis:

FAB-MS (m/Z): 1,609 (M+) (C$_{74}$H$_{81}$O$_{37}$) UV spectrum (λ$_{max}$nm, log ε, pH 6.5): 237(4.57), 310(4.64), 508(4.16), 543(4.34), 584(4.44)

The structure of (Id) was determined from the above analysis data and the results of alkaline hydrolysis and acidic partial hydrolysis.

EXAMPLE 4

One kilogram of fresh leaves of Rhoeo spathaceae W. T. Stearn was processed in the same way as in Example 1 to obtain a novel acylated anthocyanin (Ie), the principal pigment component of the material:

[3-0-{6-0-(5-0-E-ferulyl-α-L-arabinofuranosyl)-β-D-glucopyranosyl)-7-0-(6-0-E-ferulyl-β-D-glucopyranosyl)-3'-0-(6-0-E-ferulyl-β-D-glucopyranosyl)cyanidin].

Analysis: FAB-MS (m/Z): 1,433 (M+) (C$_{68}$H$_{73}$O$_{34}$)

UV spectrum (λ$_{max}$nm, log ε, pH 6.5): 236(4.53), 312(4.54), 508(4.16), 544(4.41), 588(4.45)

The structure of (Ie) was similarly determined from the analysis data and the results of alkaline hydrolysis and acidic partial hydrolysis.

All products obtained in Examples 1–4 had attractive colors which are generally red in acidic conditions.

EXAMPLE 5

The stability of the novel acylated anthocyanins of the invention was compared with that of 3-0-{6-0-α-L-arabinofuranosyl)-β-D-glucopyranosyl}-7-0-(β-D-glucopyranosyl)-3'-0-(β-D-glucopyranosyl)cyanidin which has a structure corresponding to the compound of Example 1 except that it has no acyl group. These anthocyanins were dissolved in a 1/30 M phosphate buffer at pH 6.5 and kept at 20° C. As can be seen from the results given in FIG. 1, the anthocyanins of the invention had a superior stability over the comparative anthocyanin since the former showed no discoloration as measured by the absorbancy at λ$_{max}$ for over 120 minutes.

I claim:

1. A substantially pure acylated anthocyanin of the formula (I):

wherein R$^1$ and R$^2$ may be the same or different and each represents a hydrogen atom, a ferulyl group or a caffeyl group; R$^3$ and R$^4$ may be the same or different and each represents a ferulyl group or a caffeyl group; and ANION represents an anion; and wherein said acylated anthocyanin was extracted from fruits, leaves, stems or whole plants containing said acylated anthocyanin.

2. An acylated anthocyanin according to claim 1, wherein each of the symbols R$^1$, R$^2$, R$^3$ and R$^4$ in the formula (I) represents a caffeyl group.

3. 3-0-{2,5-di-0-E-caffeyl-α-L-arabinofuranosyl)-β-D-glucopyranosyl}-7-0-(6-0-E-caffyl-β-D-glucopyranosyl)-3'-0-(6-0-E-caffeyl-β-D-glucopyranosyl)cyanidin according to claim 1.

4. 3-0-{6-0-(5-0-E-caffeyl-α-L-arabinofuranosyl)-β-D-glucopyranosyl}-7-0-(6-0-E-caffeyl-β-D-glucopyranosyl)-3'-0-(6-0-E-caffeyl-β-D-glucopyranosyl)cyanidin according to claim 1.

5. 3-0-{6-0-(2-0-E-caffeyl-α-L-arabinofuranosyl)-β-D-glucopyranosyl}-7-0-(6-0-E-caffeyl-⊖-D-glucopyranosyl)-3'-0-(6-0-E-caffeyl-β-D-glucypuranosyl)cyanidin according to claim 1.

6. 3-0-{6-0-(2,5-di-0-E-ferulyl-α-L-arabinofuranosyl)-β-D-glucopyranosyl}-7-0-(6-0-E-ferulyl-β-D-glucopyranosyl)-3'-0-(6-0-E-ferrulyl-β-D-glucopyranosyl)cyanidin according to claim 1.

7. 3-0-{6-0-(5-0-E-ferrulyl-α-L-arabinofuranosyl)-β-D-glucopyranosyl}-7-0-(6-0-E-ferulyl-β-D-glucopyranosyl)-3'-0-(6-0-E-ferulyl-β-D-glucopyranosyl)cyanidin according to claim 1.

8. An acylated anthocyanin according to claim 1, wherein said extraction is conducted at a pH which is lower than about 3.5.

9. An acylated anthocyanin according to claim 1, wherein said fruits, leaves, stems or whole plants originate from Zebrina purpusii Bruecken, Zebrina pendula Schnitzlein, Setcreasea purpurea Boom or Rhoeo spathaceae W.T. Stearn.

* * * * *